United States Patent
Dollat et al.

(10) Patent No.: US 8,652,547 B2
(45) Date of Patent: Feb. 18, 2014

(54) PROCESS FOR PREPARING GRANULES OF HYDROPHILIC ACTIVE PRINCIPLE BY EXTRUSION

(75) Inventors: Jean-Marie Dollat, Montlucon (FR); Véronique Chiavazza, Caluire (FR)

(73) Assignee: Adisseo France S.A.S., Antony (FR)

( * ) Notice: Subject to any disclaimer, the term of this patent is extended or adjusted under 35 U.S.C. 154(b) by 998 days.

(21) Appl. No.: 11/667,543

(22) PCT Filed: Dec. 14, 2005

(86) PCT No.: PCT/FR2005/003133
§ 371 (c)(1),
(2), (4) Date: Jun. 7, 2007

(87) PCT Pub. No.: WO2006/064127
PCT Pub. Date: Jun. 22, 2006

(65) Prior Publication Data
US 2007/0292576 A1    Dec. 20, 2007

(30) Foreign Application Priority Data

Dec. 15, 2004    (FR) .................... 04 13347

(51) Int. Cl.
| A23K 1/18 | (2006.01) |
| A23B 4/03 | (2006.01) |
| A23B 4/044 | (2006.01) |
| C12C 3/02 | (2006.01) |
| A23L 1/18 | (2006.01) |
| A23P 1/00 | (2006.01) |
| A23L 1/00 | (2006.01) |

(52) U.S. Cl.
USPC ............... 426/2; 426/443; 426/448; 426/516; 426/807; 424/438

(58) Field of Classification Search
USPC ............................................ 426/2, 602, 603
See application file for complete search history.

(56) References Cited

U.S. PATENT DOCUMENTS

| 4,012,535 A * | 3/1977 | Fiala et al. .................... 426/658 |
| 4,196,187 A | 4/1980 | Dannelly et al. |
| 4,696,914 A | 9/1987 | Rüsse et al. |
| 4,780,315 A | 10/1988 | Wu et al. |
| 4,842,863 A * | 6/1989 | Nishimura et al. ........... 424/438 |
| 4,996,067 A * | 2/1991 | Kobayashi et al. ............. 426/96 |
| 5,190,775 A | 3/1993 | Klose |
| 5,225,238 A | 7/1993 | Ardaillon et al. |
| 5,244,669 A * | 9/1993 | Satoh et al. .................... 424/438 |
| 5,279,832 A | 1/1994 | Greissinger et al. |
| 5,290,560 A | 3/1994 | Autant et al. |
| 5,296,219 A | 3/1994 | Ardaillon et al. |
| 5,474,971 A * | 12/1995 | Sandell .......................... 504/367 |
| 5,540,932 A * | 7/1996 | Lanter et al. ................... 424/442 |
| 5,660,769 A | 8/1997 | Sagar et al. |
| 5,863,586 A * | 1/1999 | Johnsen et al. ............... 426/438 |
| 5,874,102 A * | 2/1999 | LaJoie et al. .................. 424/438 |
| 6,174,548 B1 | 1/2001 | Chen et al. |
| 6,238,727 B1 * | 5/2001 | Takemoto et al. ............ 426/656 |
| 6,306,427 B1 * | 10/2001 | Annonier et al. ............. 424/438 |
| 6,337,084 B1 * | 1/2002 | Stevens et al. ................ 424/442 |
| 6,500,426 B1 | 12/2002 | Barendse et al. |
| 2002/0068088 A1 | 6/2002 | Gruber |
| 2002/0110877 A1 | 8/2002 | Bathe et al. |
| 2003/0129295 A1 | 7/2003 | Richardson |
| 2003/0165611 A1 | 9/2003 | Chiavazza et al. |
| 2004/0048814 A1 | 3/2004 | Vanderbist et al. |
| 2004/0053884 A1 | 3/2004 | Nakagiri et al. |
| 2004/0115304 A1 | 6/2004 | Dubner et al. |
| 2004/0173923 A1 | 9/2004 | Schutz et al. |

FOREIGN PATENT DOCUMENTS

| EP | 0 246 310 B1 | 11/1987 |
| EP | 0 351 760 A2 | 1/1990 |
| EP | 0 437 388 A1 | 7/1991 |
| EP | 0 447 298 A1 | 9/1991 |
| EP | 0 462 015 A1 | 12/1991 |
| EP | 1177726 A1 * | 2/2002 |
| EP | 1 356 811 A1 | 10/2003 |
| EP | 1 405 570 A1 | 4/2004 |
| FR | 2 663 818 A1 | 1/1992 |

(Continued)

OTHER PUBLICATIONS

"Hydrophilicity", Creighton, Thomas C. (1999). Encyclopedia of Molecular Biology, vols. 1-4.*

(Continued)

*Primary Examiner* — Rena Dye
*Assistant Examiner* — Assaf Zilbering
(74) *Attorney, Agent, or Firm* — Oliff PLC

(57) ABSTRACT

The present invention relates to a process for preparing cores of granules intended for animal nutrition, the said cores comprising:
 a hydrophilic active principle present in an active content of greater than or equal to 60% by weight,
 at least one meltable binder,
 at least one plasticizer,
the said process comprising (a) a first step of mixing of the ingredients, (b) a second step of extrusion of the mixture through an extruder, especially a single-screw or twin-screw extruder, equipped with one or more dies, so as to obtain rods, and (c) a third step of spheronization of the rods, the said process being characterized in that a preliminary dry co-grinding of the ingredients is performed before extruding the mixture, the said co-grinding being performed at a temperature of not more than 50° C. The present invention also relates to a process for preparing granules of hydrophilic active principle comprising the said cores.

15 Claims, No Drawings

(56) References Cited

FOREIGN PATENT DOCUMENTS

| JP | A-55-099164 | | 7/1980 |
|---|---|---|---|
| WO | WO 0142221 A1 | * | 6/2001 |
| WO | WO 02/10208 A1 | | 2/2002 |
| WO | WO 03/079809 A1 | | 10/2003 |

OTHER PUBLICATIONS

Almeida Prieto et al., Starch—Dextrin Mixtures as Base Excipients for Extrusion—Spheronization Pellets. Available online at http://apv-mainz.de on Dec. 9, 2004.*

Pet Treats. Available online at www.ifcfiber.com on Jan. 31, 2001.*

Sep. 25, 2009 Office Action issued in corresponding Chinese Patent Application No. 2005800420153 (with translation).

Apr. 26, 2006 International Search Report issued in International Patent Application No. PCT/FR2005/003132.

Sep. 16, 2011 Office Action issued in U.S. Appl. No. 11/667,445.

Apr. 14, 2011 Office Action issued in U.S. Appl. No. 11/667,445.

Jul. 22, 2010 Office Action issued in U.S. Appl. No. 11/667,445.

U.S. Appl. No. 11/667,445 in the name of Dollat et al., filed Jun. 21, 2007.

Apr. 10, 2012 Office Action issued in U.S. Appl. No. 11/667,445.

* cited by examiner

PROCESS FOR PREPARING GRANULES OF HYDROPHILIC ACTIVE PRINCIPLE BY EXTRUSION

The present invention relates to a process for preparing cores of granules of hydrophilic active principle. The present invention also relates to a process for preparing granules of hydrophilic active principle intended for ruminant nutrition or treatment.

Certain compounds, for example vitamins, mineral salts and amino acids, are essential in the diet of ruminants since they are limiting in the daily nutritional intake. The diet of ruminants is thus generally supplemented with these compounds.

When they are administered orally to ruminants, these substances are destroyed in the rumen via the action of the digestive enzymes. Thus, in order to be beneficial to and assimilable by the animals, these substances are protected with a coating that allows them to pass through the rumen without damage and to be broken down in the abomasum, so as to release the active substance in the intestine.

It is known practice to prepare granules suitable for administration to ruminants and these granules are generally composed of a core of active substance and a coating that is resistant to the neutral pH of the rumen and degradable at the more acidic pH of the abomasum.

One of the possibilities for preparing active principle cores consists in performing a melt-extrusion. The extrusion machines are machines that use both heat and pressure, by forcing the mixture to be extruded through a die. During this step, the active ingredients undergo an irreversible degradation.

To solve this problem, it is common to seek to modify the composition of the granules. For example, patent FR 2 663 818 proposes the use of a meltable binder. In this respect, use is generally made of a fatty substance, for example stearic acid. These fatty substances have the advantage of mixing readily with hydrophobic active principles.

However, when it is a matter of mixing a hydrophilic active principle present in high content with one of the known meltable binders, homogenization difficulties are encountered.

The present invention seeks to allow the easy extrusion of hydrophilic active principles.

The inventors have realized, surprisingly, that by adding a step of co-grinding of the ingredients to the extrusion process, this objective is achieved.

Patent FR 2 663 818, discussed above, does not describe a preliminary step of co-grinding of the ingredients.

Patent application WO 03/079 809 relates to pellets with a high proportion of fat.

The present invention thus relates to a process for preparing cores of granules intended for animal nutrition, the said cores comprising:
a hydrophilic active principle present in an active content of greater than or equal to 60% by weight,
at least one meltable binder,
at least one plasticizer,
the said process comprising (a) a first step of mixing of the ingredients, (b) a second step of extrusion of the mixture through an extruder, especially a single-screw or twin-screw extruder, equipped with one or more dies, so as to obtain rods, and (c) a third step of spheronization of the rods, the said process being characterized in that a preliminary dry co-grinding of the ingredients is performed before extruding the mixture, the said co-grinding being performed at a temperature of not more than 50° C.

The term "hydrophilic active principle" means any hydrophilic substance with established physiological activity in the animal. Especially included in the category of active principle according to the invention are feed supplements. Animal feed supplements are products intended to be ingested, as a supplement to the common diet, in order to overcome the insufficiency of the daily intake of certain compounds. It is known practice, for example, in general, to supplement the feed rations of reared animals with active principles, so as to increase the zootechnical performance of the reared animals. These may especially be vitamins, mineral salts, amino acids, trace elements, hormones or antibiotics.

Advantageously, the hydrophilic active principle is an amino acid. Even more preferably, it is chosen from the group consisting of lysine, arginine and tyrosine, and salts and esters thereof. As a guide, the hydrophilic active principle is L-lysine or its commercial form: L-lysine hydrochloride. It may also be L-arginine hydrochloride or L-tyrosine hydrochloride.

The hydrophilic active principle is also present in an active content of greater than or equal to 60% by weight of the granule core. Advantageously, the hydrophilic active principle is present in an active content of greater than or equal to 64% by weight of the granule core.

The term "active content" means the real content of active principle itself, i.e. the active principle in the base form having the physiological activity in the animal whose effect is sought. It may be the form that is fully assimilated by the animal's body. The reason for this is that the active principles may be in a commercial form that is more advantageous and easier to handle than the active form. This is especially the case when the active principle is in the form of a salt or analogue. It results therefrom that, if it is decided to use a commercial form of the active principle that is different from the active principle itself, a person skilled in the art must calculate the weight equivalence, the real active content of active principle. This active content may represent, for example, a certain percentage of the content of active form, belonging to the starting compound mixture.

The granule core also comprises at least one meltable binder. The meltable binder is selected from the group consisting of polyethylene glycol waxes, paraffins, oils or fats, fatty acids containing from 10 to 32 carbon atoms, the corresponding mono-, di- and triesters, and the corresponding alcohols. As a guide, it may especially be stearic acid. Mention may also be made of PRECIROL® and COMPRITOL®.

The granule cores according to the present invention also comprise at least one plasticizer. This plasticizer is preferentially chosen from cellulose or its derivatives, and especially ethylcellulose.

The present invention thus relates to an extrusion process characterized in that it comprises a preliminary step of dry co-grinding of the ingredients, the said co-grinding being performed at a temperature of not more than 50° C.

The term "grinding" more particularly means the mechanical action that consists in reducing the starting ingredients to a given size. The term "co-grinding" implies the grinding of several ingredients at the same time.

The co-grinding is thus performed "dry", i.e. all the ingredients are in dry form, usually in powder form. To perform the co-grinding according to the present invention, it is not necessary to add a liquid ingredient to the mixture, or to dissolve one or all of the ingredients.

According to the present invention, the co-grinding is performed at a temperature of not more than 50° C.

The constituent ingredients of the granule cores are in the form of powders. The object of the co-grinding step is to reduce the sizes of these ingredients via a mechanical treatment. The co-grinding of the ingredients before extrusion also has the advantage of improving the dispersion of the constituents in the mixture.

Co-grinding thus has a twofold benefit: it reduces the size of the ingredients, and it simultaneously increases the homogeneity of the mixture, i.e. it also allows uniform distribution of the ingredients in the mixture.

According to the present invention, the ingredients thus undergo a co-grinding step before extrusion. The co-grinding of the ingredients requires the use of a mill, which may be chosen especially from knife mills, rotor mills, bar mills, grate mills, disc mills or ball mills. The choice of mill depends mainly on the expected particle size distribution of the ground product.

According to the present invention, a jacketed mill in which circulates a stream of water may also be used, so that the co-grinding is performed at a temperature of not more than 50° C., i.e. less than or equal to 50° C. Another possibility consists, for example, in cooling the mill with liquid nitrogen or in cardice, the object being for this essential step of the process to be performed at a temperature not exceeding 50° C.

According to the present invention, the particle size requirements of the ground product are as follows:

| Particle size of the ground product | Percentage in the mixture |
| --- | --- |
| Greater than 400 μm | 0% |
| Greater than 200 μm | ≤15%, preferably ≤10% |
| Between 100 and 200 μm | ≤50%, preferably ≤20% |
| Less than 100 μm | ≥50%, preferably ≥75% |
| Less than 50 μm | ≤50% |

Advantageously, the median diameter of the particles of the ground product is between 50 and 100 μm. The term "median diameter" means the size of the particles of the ground product of which 50% of the sample has a smaller size and 50% of the sample has a larger size. In the present case, the median diameter is between 50 and 100 μm.

The cores of the granules of the present invention may also comprise a starch. The term "starch" means any polysaccharide formed from the combination of two polymers: amylose and amylopectin. According to the present invention, the starch may be in powder form or in paste form. As a guide, it may be native wheat starch, native corn starch, native rice starch or potato starch. It may also be the same starches treated physically, for example pregelatinized.

A disintegrant that accelerates the breakdown of the tablet in the digestive tract may also be added to the granule cores. This disintegrant may especially be talc, silica, carbonate or polyphosphate, for example $Na_2O$, $CaO$, $P_2O_5$ or $Al_2O_3$.

The cores may also comprise another active principle.

The term "other active principle" means any substance having an established physiological activity in the animal. Especially included in the category of active principle according to the invention are feed supplements. Animal feed supplements are products intended to be ingested, as a supplement to the common diet, in order to overcome the insufficiency of the daily intake of certain compounds. It is known practice, for example, in general, to supplement the feed rations of reared animals with active principles, so as to increase the zootechnical performance of the reared animals. These may especially be vitamins, mineral salts, amino acids, trace elements, hormones or antibiotics.

Advantageously, the said active principle is an amino acid. As a guide, mention may be made of methionine, tryptophan or 2-hydroxy-4-methylthiobutanoic acid (hydroxy analogue of methionine), which has the advantage of being in liquid form, which facilitates its use by the feed-producing companies. Mention may also be made of the salts and esters of these compounds.

The said other active principle is preferentially present in a very low active content, of less than or equal to 1% by weight of the granule core.

According to the present invention, the granule core comprises an active content of active principles, i.e. the hydrophilic active principle and possibly at least one other active principle, of greater than 64% by weight of the granule core.

Preferentially, the meltable binder is stearic acid and its content in the granule cores is not more than 12% by weight of the composition of the granule cores of the present invention.

The extrusion process according to the present invention more particularly comprises the following steps:
mixing of the ingredients;
co-grinding;
extrusion;
spheronization; and
coating.

The ingredients are first mixed together and are then co-ground.

It is also possible, according to the present invention, to add water to the mixture after co-grinding and before extrusion. As a guide, less than 10% of water by weight of the mixture before extrusion is added. Preferably, between 3% and 5% of water by weight of the mixture before extrusion is added. Thus, the granule cores obtained after the process may also contain a certain amount of water.

The particle size of the ingredients after the co-grinding step allows the melt-extrusion of the ingredients comprising a high content of hydrophilic active principle and consequently a better extrusion rate or "extrudability".

The mass to be extruded is then forced through an extruder, preferably a single-screw or twin-screw extruder, equipped with one or more dies having orifices of the desired granule diameter.

The quality of the extrudates is evaluated by means of a friability test.

After extrusion, the rods undergo a spheronization step, the object of which is to make the rods spherical, without irregularities or surface roughness (as smooth as possible).

It is also important to point out that the quality of the coating step that follows, and thus of the protection of the active principle, lies mainly in the spheronization step.

In a subsequent step, the spheronized granule cores are coated so as to obtain protected granules. The coating step proceeds in accordance with the teaching described in patents EP 462 01 5 and EP 447 298, via a composition based on a pH-sensitive polymer. This composition has many advantages and in particular it is not degraded in the rumen, but may be released in the abomasum and/or the intestine.

The coating process comprises a first step of polymerization of monomers in aqueous emulsion, a second step of preparation of the coating emulsion and a third step of deposition of the said aqueous emulsion onto the active principle cores.

As a guide, the pH-sensitive polymers, which are prepared by aqueous-emulsion polymerization, are chosen from:
polyvinyl acetals of acetylacetic esters substituted with dialkyl nitrogen groups such as the diethylamino group, copolymers of styrene or of acrylonitrile with vinylpyridine isomers or derivatives, and
chitosan salts.

The copolymer based on styrene and on 2-vinylpyridine is preferably used.

The polymer is prepared by placing the monomer(s) in contact with a surfactant and a polymerization initiator.

The surfactants are preferably chosen from the alkaline salts of fatty acids, for example the sodium salt of oleic acid and the sodium salt of stearic acid.

The polymerization initiator is chosen from the soluble initiators conventionally used in emulsion processes, for example sodium persulfate. The pH during the polymerization is preferably set at between 10 and 14.

Once the aqueous emulsion has been performed, the coating emulsion is prepared. An aqueous emulsion containing the pH-sensitive polymer obtained in the preceding step, and a hydrophobic substance, are preferably used as coating composition.

The hydrophobic substance is especially chosen from fatty acids containing 12 to 22 carbon atoms, esters thereof and salts thereof (especially mono-, di- and triesters). It may especially be stearic acid.

The aqueous emulsion may also contain additives such as antistatic agents, fungicides, plasticizers, dyes, appetence agents, for example, olfactory additives, and additional emulsifiers.

The emulsion is then deposited onto the cores to be coated. For example, this emulsion is sprayed onto the active principle granules.

It is also important to point out that, in the context of the present invention, the contents are expressed as weight percentages of the granule core or, depending on the case, as weight percentages of the granule itself. Owing to the presence of the coating, this percentage differs from the weight percentage of the granule core and a person skilled in the art should thus calculate this new percentage.

In the case of a hydrophilic active principle present in an active content of greater than or equal to 60% by weight of the granule core, and in the situation of a coating representing 15% by weight of the granule, the hydrophilic active principle is present, in an equivalent manner in the granule itself, in an active content of greater than or equal to 51% by weight of the granule.

The process covered by the present invention advantageously leads to granule cores with an active content of hydrophilic active principle of greater than or equal to 64% by weight of the granule core, or, in the same situation as previously (i.e. a coating representing 15% by weight of the granule), to an active content of greater than 54.4% by weight of the granule.

Also, the cores of the present invention may comprise another active principle. This active principle is preferentially present in a very low active content, of less than or equal to 1% by weight of the granule core.

In the situation of a coating representing 15% by weight of the granule, this other active principle is present, in an equivalent manner, in an active content of less than or equal to 0.85% by weight of the granule itself.

The present invention also relates to granule cores and granules, intended for animal nutrition, in particular for the feed of ruminants, which may be obtained via the process of the present invention.

The granules of hydrophilic active principle obtained via the process of the present invention have many advantages. Among these, and as emerges on reading the examples that follow, are especially industrially exploitable degrees of protection and degrees of release, whereas it is not possible to obtain granules with a high content of active principle via an extrusion process not comprising a preliminary step of co-grinding of the ingredients.

The conditions of the tests performed to determine the degrees of protection and release of the active principles in the granules of the present invention are as follows:

Degree of Release (In Vitro Test)

This is represented by the percentage fraction of the active principle dissolved from the protected form, after a residence time of 2 hours with stirring in an aqueous medium maintained at pH 2 (potassium sulfate and 2N sulfuric acid to permanently maintain the pH at 2) and 40° C., under standardized conditions.

As a guide, the degree of release of granules containing methionine is measured under these conditions by iodometry, whereas that of lysine is measured by argentimetry. In general, HPLC or any other chromatographic method (especially ion exchange) is used.

Degree of Protection (In Vitro Test)

This is represented by the percentage fraction of the amino acid not released from the protected form, after a residence time of 24 hours with stirring in a buffer solution at pH 6.0 (phosphoric acid/dipotassium phosphate) and 40° C., under standardized conditions.

As a guide, the degree of protection of granules containing methionine is measured under these conditions by iodometry, whereas that of lysine is measured by argentimetry. In general, HPLC or any other chromatographic method (especially ion exchange) is used. The degree of protection is deduced therefrom by difference (difference between the amount of active principle introduced and the amount of active principle released).

The quality of extrudates obtained is also evaluated. A friability test is performed, on a Sotax Friabilitor USP F1 machine, with 10 g of extrudates for 5 minutes at 50 rpm. The friability is given by the following formula: (initial weight−weight of rods recovered after the test)/initial weight.

The appearance of the granules obtained by the process of the present invention, more particularly their size and their shape, is very important.

The choice of the size of the granules depends directly on the zootechnical application. It is generally imposed by physiological reasons, for example to avoid the process of remastication by the ruminants.

The spheronized granule cores should be round, spherical and free of roughness (as smooth as possible), such that the coating step proceeds under the best conditions, and such that the active principle is correctly and uniformly protected.

The examples and tables below will enable some of the advantages and characteristics of the present invention to be demonstrated.

The inventors realized that the extrusion of a mixture having an active content of hydrophilic active principle, and especially lysine, of greater than or equal to 60% by weight, without the use of a preliminary step of co-grinding of the ingredients before extruding the mixture, was made very difficult and risked damaging the equipment.

This step is thus essential to the extrudability of a mixture comprising a high content of hydrophilic active principle.

The following examples thus all comprise a step of co-grinding of the ingredients before extrusion.

COMPARATIVE EXAMPLE

Methionine Granules 895 g of methionine, 100 g of stearic acid and 5 g of ethylcellulose are introduced into the cylindroconical tank of a Böhle mixer (model LM 40) and mixed together.

After mixing together the three constituents, the particle size distribution of the mixture is as follows:

| Size of the particles of the ground product | Percentage in the mixture |
|---|---|
| Greater than 400 μm | 18.1% |
| Greater than 200 μm | 23.7% |
| Between 100 and 200 μm | 20.7% |
| Between 50 and 100 μm | 15.8% |
| Less than 50 μm | 21.7% |

The mixture is then extruded through a Bivis Haake Rheomex TW 100 machine configured with two counter-rotating screws (diameter 19.7 mm and length 331 mm) and a nine-hole die (2 mm in diameter).

The extrudability is effective on this mixture of relatively coarse particle size. The extrusion of a mixture with a methionine content of greater than 60% by weight, without the use of a preliminary step of co-grinding of the ingredients before extruding the mixture, is possible, in contrast with the mixtures of the present invention, i.e. mixtures comprising a high active content of hydrophilic active principle.

The extrusion rate is about 2 kg/h.

The friability of the extrudates is measured: it is about 1.1%.

Their apparent density is between 0.647 and 0.648 g/cm³.

The extrudates thus obtained are therefore of satisfactory quality.

In addition, co-grinding of the three constituents of this formulation (methionine, stearic acid and ethylcellulose) to adjust to the particle size distribution of the lysine-based mixtures covered by the present invention would not provide any further advantage. In contrast, the inventors realized that in the present case such particle size distributions increase the friability of the extrudates.

EXAMPLE 1

Lysine Granules

The equipment used is as follows:
a Böhle mixer with a rotating cylindroconical tank, model LM 40;
a Retsch laboratory grate mill;
a Bivis Haake Rheomex TW 100 extruder configured with two counter-rotating screws (diameter 19.7 mm and length 331 mm) and a nine-hole die (2 mm in diameter);
a "Wyss-Probst engineering" spheronizer (300×100 mm tank) with circulation of thermostatically-maintained oil in the jacket; and
a UniGlatt mini fluid bed (2 L tank equipped with a "Würster" nozzle).

The friability test is performed on a Sotax friabilator USP F1 with 10 g of extrudates, for 5 minutes at 50 rpm.

The operating conditions are as follows:

800 g of lysine hydrochloride, 180 g of stearic acid and 20 g of ethylcellulose are introduced into the tank of the Böhle mixer, and mixed together for 15 minutes at 50 rpm.

This mixture is then co-ground on a 1 mm grate at speed 1. The co-grinding is performed at a temperature not exceeding 50° C.

The particle size of the mixture leaving the laboratory grinder is such that a powder is obtained with 50% of particles <50 μm in size and less than 10% of particles >200 μm in size.

On leaving the mill, the mixture obtained is rehomogenized using the Bbhle mixer for 15 minutes, still at 50 rpm.

This mixture is introduced via a hopper into the Bivis extruder, the temperatures in the three sections of which have been preset to:
72° C. in the feed compartment;
78° C. in the intermediate compartment; and
80° C. in the compartment before the die.

The extrusion rate is about 1 kg/h.

The extrudates obtained are chopped to a length of 2 mm. They are then characterized in terms of friability.

The friability of the extrudates is measured: it is between 1.5 and 2%.

The extrudates are then spheronized at 500 rpm, for 8 minutes and at 90° C., and are then screened between 1.4 and 2.5 mm. The yield of this operation is 87%.

The screened extrudates are then coated using the emulsion prepared by stirring with a polytron blender at a temperature of between 75 and 90° C. The emulsion, with a solids content of 25%, has the following composition:
stearic acid: 20%
copolymer of 2-vinylpyridine and of styrene at 20% solids: 24.96%
water: 55%
solid sodium hydroxide: 0.04%

The spraying rate is 10 g/min and the yield is 98%.

After deposition of the coating agent, the extrudates are characterized in terms of degree of protection and degree of release of lysine.

For a degree of coating of 14.6%, the content of base lysine is 54.2%, the degree of protection measured in vitro ranges between 61% and 89%, and the degree of release is 95%.

| % Degree of coating | % Content of base lysine | % Degree of protection in vitro | % Degree of release |
|---|---|---|---|
| 14.6 | 54.2 | 61 to 89 | 95 |

EXAMPLE 2

Lysine Granules

Example 1 is repeated with the same apparatus, but replacing some of the stearic acid with standard native cornstarch.

800 g of lysine hydrochloride, 120 g of stearic acid, 60 g of standard cornstarch and 20 g of ethylcellulose are thus mixed together.

The mixture is co-ground in a manner identical to that of Example 1.

The particle size distribution of the mixture leaving the laboratory mill is such that a powder is obtained with 50% of particles <50 μm and less than 10% of particles >200 μm.

The stearic acid assay (average of 1.3 measurements) gives 11.80% for a theoretical value of 12%.

The mixture is then extruded under the following conditions:
72° C. in the feed compartment;
75° C. in the intermediate compartment; and
78° C. in the compartment before the die.

The extrusion rate is about 2 kg/h.

It may also be noted that the extrusion rate is better than that of Example 1, in which starch is not used. It may thus be envisaged to double the production efficiency by using starch. This is an advantageous characteristic of the present invention.

The extrudates obtained are chopped to a length of 2 mm and then characterized in terms of friability.

The friability of the extrudates is measured: it is between 0.5% and 0.8%.

It is interesting to note that the friability of the extrudates comprising lysine and starch is better than that of the extrudates comprising lysine alone (Example 1).

The extrudates are then spheronized at 500 rpm, for 6 minutes and at 90° C., and then screened between 1.4 and 2.5 mm. The yield for this operation is 88%.

Two degrees of coating, of 15% and 16%, respectively, were performed on this batch of extrudates. The spraying rate is 10 g/min and the yields are 98% and 97%.

The product quality results are collated in the table below.

| % Degree of coating | % Content of base lysine | % Degree of protection in vitro | % Degree of release |
|---|---|---|---|
| 14.6 | 56 | 96 | 100 |
| 16.4 | 55.2 | 99 | 100 |

EXAMPLE 3

Lysine Granules

Example 2 is repeated with the same apparatus, but replacing the cornstarch with wheat starch.

800 g of lysine hydrochloride, 120 g of stearic acid, 60 g of wheat starch and 20 g of ethylcellulose are thus mixed together.

The mixture is co-ground under the same conditions as those of Example 2 and extruded under the following conditions:

72° C. in the feed compartment;
75° C. in the intermediate compartment; and
78° C. in the compartment before the die.

The extrusion rate is about 1.4 kg/h.

The extrusion rate is also better than that of Example 1, in which starch is not used.

The extrudates obtained are chopped to a length of 2 mm and then characterized in terms of friability.

The friability of the extrudates is between 0.6% and 1%.

The extrudates are then spheronized at 500 rpm for 7 minutes and at 90° C., and then screened between 1.4 and 2.5 mm. The yield for this operation is 85%.

As regards the coating, the spraying rate is 10 g/min and the yield is 98%.

For a degree of coating of 14.6%, the base lysine content is 56.2%, the degree of protection measured in vitro is 88% and the degree of release is 100%.

| % Degree of coating | % Content of base lysine | % Degree of protection in vitro | % Degree of release |
|---|---|---|---|
| 14.6 | 56.2 | 88 | 100 |

EXAMPLE 4

Lysine Granules

Example 2 is repeated with the same apparatus, but replacing the cornstarch with potato starch.

800 g of lysine hydrochloride, 120 g of stearic acid, 60 g of potato starch and 20 g of ethylcellulose are thus mixed together.

The mixture is co-ground under the same conditions as those of Example 2 and extruded under the following conditions:

73° C. in the feed compartment;
75° C. in the intermediate compartment; and
79° C. in the compartment before the die.

The extrusion rate is about 1.5 kg/h.

The extrusion rate is also better than that of Example 1, in which starch is not used.

The extrudates obtained are chopped to a length of 2 mm and then characterized in terms of friability.

The friability of the extrudates is between 0.5% and 0.7%.

The extrudates are then spheronized at 500 rpm for 6 minutes and at 90° C., and then screened between 1.4 and 2.5 mm. The yield for this operation is 89%.

As regards the coating, the spraying rate is 10 g/min and the yield is 99%.

For a degree of coating of 14.6%, the base lysine content is 56.2%, the degree of protection measured in vitro is 96% and the degree of release is 100%.

| % Degree of coating | % Content of base lysine | % Degree of protection in vitro | % Degree of release |
|---|---|---|---|
| 14.6 | 56.2 | 96 | 100 |

EXAMPLE 5

Lysine Granules

Example 2 is repeated with the same apparatus, but replacing the cornstarch with Arbocel cellulose.

800 g of lysine hydrochloride, 120 g of stearic acid, 60 g of Arbocel cellulose and 20 g of ethylcellulose are thus mixed together.

The mixture is co-ground under the same conditions as those of Example 2 and extruded under the following conditions:

73° C. in the feed compartment;
75° C. in the intermediate compartment; and
75° C. in the compartment before the die.

The extrusion rate is about 0.5 kg/h.

The extrudates obtained are chopped to a length of 2 mm and then characterized in terms of friability.

The friability of the extrudates is between 1.5% and 2%.

The extrudates are then spheronized at 500 rpm for 6 minutes and at 90° C., and then screened between 1.4 and 2.5 mm. The yield for this operation is 88%.

As regards the coating, the spraying rate is 10 g/min and the yield is 98%.

For a degree of coating of 16.4%, the base lysine content is 53.4%, the degree of protection measured in vitro is 89% and the degree of release is 100%.

| % Degree of coating | % Content of base lysine | % Degree of protection in vitro | % Degree of release |
|---|---|---|---|
| 16.4 | 53.4 | 89 | 100 |

EXAMPLE 6

Lysine and Methionine Granules

Example 2 is repeated with the same apparatus, but incorporating 0.35% of methionine at the expense of the stearic acid.

800 g of lysine hydrochloride, 3.5 g of methionine, 116.5 g of stearic acid, 60 g of cornstarch and 20 g of ethylcellulose are thus mixed together. The mixture is co-ground under the same conditions as those of Example 2 and extruded under the following conditions:

72° C. in the feed compartment;
75° C. in the intermediate compartment; and
78° C. in the compartment before the die.

The extrusion rate is about 1.6 kg/h.

The extrudates obtained are chopped to a length of 2 mm and then characterized in terms of friability.

The friability of the extrudates is between 0.4% and 0.6%.
Their apparent density is between 0.62 and 0.64 g/cm$^3$.
The true density calculated for the granules is 1.24 g/cm$^3$.

The extrudates are then spheronized at 500 rpm for 8 minutes and at 90° C., and then screened between 1.4 and 2.5 mm. The yield for this operation is 92%.

As regards the coating, the spraying rate is 11 g/min and the yield is 96%.

For a degree of coating of 15%, the base lysine content is 55%, the degree of protection measured in vitro is 96% and the degree of release is 100%.

| % Degree of coating | % Content of base lysine | % Degree of protection in vitro | % Degree of release |
| --- | --- | --- | --- |
| 15 | 55 | 96 | 100 |

EXAMPLE 7

Lysine and Methionine Granules

The equipment used is as follows:
a 3000 liter industrial band mixer;
a Contraplex industrial disc mill;
a Clextral industrial twin-screw extruder, model Evolum 53 with 2 co-rotating screws (L/D=24), 6 sleeves set at 60, 80, 80, 80, 70 and 70° C. of feed to the die, a straight die with two times 6 holes (length 12 mm, diameter 2 mm, L/D=6) and a 4-blade knife;
a "Wyss-Probst engineering" spheronizer (300×100 mm tank) with circulation of thermostatically maintained oil in the jacket; and
a UniGlatt mini fluid bed (2 L tank equipped with a "Würster" nozzle).

The friability test is performed on a Sotax friabilator USP F1 performed with 10 g of extrudates for 5 minutes at 50 rpm.

The operating conditions are as follows:
1025 kg of mixture containing 80% lysine hydrochloride, 0.35% methionine, 11.65% stearic acid, 6% cornstarch and 2% ethylcellulose are co-ground.

The particle size distribution of the mixture leaving the mill is such that a powder is obtained with 60% of particles having a diameter of less than 50 μm and 5% of particles having a diameter of greater than 200 μm.

The stearic acid assayed in the mixture is 12.07% (for a theoretical value of 11.65%).

This mixture serves to feed an industrial extruder operating at 60 kg/hour (screw speed 200 rpm) and at a chopping speed of 1800 rpm.

The extrusion yield, defined as the % of extrudates longer than 1.4 mm, is 99%.

The friability measured for these extrudates is between 0.5 and 0.7%.

Their apparent density is 0.62 g/cm$^3$. The true density calculated for the granules is 1.24 g/cm$^3$.

The extrudates are than spheronized at 500 rpm for 10 minutes and at 90° C., and then screened between 1.4 and 2.5 mm. The yield for this operation is 88%.

For coating conditions identical to those of Example 1 and for a degree of coating of 15%, the base lysine content is 53.8%, the degree of protection measured in vitro is 87% and the degree of release is 100%.

| % Degree of coating | % Content of base lysine | % Degree of protection in vitro | % Degree of release |
| --- | --- | --- | --- |
| 15 | 53.8 | 87 | 100 |

EXAMPLE 8

Lysine and Methionine Granules

The same equipment as that of Example 7 is used, but the extrudates are spheronized and coated on industrial equipment using:
a Caleva 700 spheronizer; and
a fluidized-bed tank of 300 liters equipped with 5 nozzles in top-spray configuration.

The operating conditions are as follows:
The procedure is performed in a manner identical to that of Example 7.

After extrusion, the extrudates are spheronized in 25 kg batches. The industrial machine 700 mm in diameter is set at 350 rpm for an extrudate temperature of 90° C. The spheronization time is 12 min. The extrusion yield, defined as the percentage of granules between 1.4 and 2.5 mm, is 83%.

The spheronized granules are then coated under the following conditions:

| | |
| --- | --- |
| Amount of charged spheronized granules: | 150 kg |
| Amount of sprayed coating: | 116.4 kg of 25% solids |
| | i.e. 29.1 kg solids |
| Real spraying rate: | 45 kg/h |
| Amount of granules obtained: | 178.8 kg |
| Theoretical amount expected: | 179.1 kg |
| Real degree of coating: | 16.2% |
| | i.e. 3.2% of copo V2P/styrene |
| Material balance: | 99.8% |

For a degree of coating of 16%, the base lysine content is 51.2%, the degree of protection measured in vitro is 94% and the degree of release is 98%.

| % Degree of coating | % Content of base lysine | % Degree of protection in vitro | % Degree of release |
| --- | --- | --- | --- |
| 16 | 51.2 | 94 | 98 |

TABLE 1

Summary table of the compositions of the granule cores

| Component | | Example 1 | Example 2 | Example 3 | Example 4 | Example 5 | Example 6 | Example 7 | Example 8 |
|---|---|---|---|---|---|---|---|---|---|
| Lysine | g | 800 | 800 | 800 | 800 | 800 | 800 | | |
| | % HCl | 80 | 80 | 80 | 80 | 80 | 80 | 80 | 80 |
| | % Base | 64 | 64 | 64 | 64 | 64 | 64 | 64 | 64 |
| Methionine | g | Abs. | Abs. | Abs. | Abs. | Abs. | 3.5 | | |
| | % | | | | | | 0.35 | 0.35 | 0.35 |
| Stearic acid | g | 180 | 120 | 120 | 120 | 120 | 116.5 | | |
| | % | 18 | 12 | 12 | 12 | 12 | 11.65 | 11.65 | 11.65 |
| Starch (or equivalent) | type | Abs. | corn | wheat | potato starch | Abs. | corn | corn | corn |
| | g | | 60 | 60 | 60 | | 60 | | |
| | % | | 6 | 6 | 6 | | 6 | 6 | 6 |
| Other | type | | | | | Arbocel cellulose | | | |
| | g | | | | | 60 | | | |
| | % | | | | | 6 | | | |
| Ethylcellulose | g | 20 | 20 | 20 | 20 | 20 | 20 | | |
| | % | 2 | 2 | 2 | 2 | 2 | 2 | 2 | 2 |
| Total weight | g | 1000 | 1000 | 1000 | 1000 | 1000 | 1000 | | |
| | or kg | | | | | | | 1025 | 1025 |

Abs. = Absent

TABLE 2

Summary table of the characteristics of the granule cores and granules

| | | Example 1 | Example 2 | | Example 3 | Example 4 | Example 5 | Example 6 | Example 7 | Example 8 |
|---|---|---|---|---|---|---|---|---|---|---|
| Starch | Type | Abs. | Corn | | Wheat | Potato starch | Abs. | Corn | Corn | Corn |
| Lysine content in the cores | % HCl | 80 | 80 | | 80 | 80 | 80 | 80 | 80 | 80 |
| | % Base | 64 | 64 | | 64 | 64 | 64 | 64 | | |
| Extrusion rate | kg/h | 1 | 2 | | 1.4 | 1.5 | 0.5 | 1.6 | 60 | 60 |
| Friability of the extrudates | % | 1.5-2 | 0.5-0.8 | | 0.6-1 | 0.5-0.7 | 1.5-2 | 0.4-0.6 | 0.5-0.7 | 0.5-0.7 |
| Degree of coating | % by weight of the granule | 14.6 | 14.6 | 16.4 | 14.6 | 14.6 | 16.4 | 15 | 15 | 16 |
| Lysine content in the granules | % Base | 54.2 | 56 | 55.2 | 56.2 | 56.2 | 53.4 | 55 | 53.8 | 51.2 |
| Degree of protection in vitro | % | 61-89 | 96 | 99 | 88 | 96 | 89 | 96 | 87 | 94 |
| Degree of release | % | 95 | 100 | 100 | 100 | 100 | 100 | 100 | 100 | 98 |

Abs. = Absent

The invention claimed is:

1. Process for preparing cores of granules intended for animal nutrition, said cores comprising a mixture of the following ingredients:
   a hydrophilic active principle present in a content of greater than or equal to 60% by weight,
   at least one meltable binder,
   at least one plasticizer, and
   a starch in an amount that increases the extrusion rate and decreases the friability of a plurality of extrudates, in comparison with cellulose when no starch is used,
   said process comprising
   (a) mixing the ingredients to obtain the mixture,
   (b) dry co-grinding the mixture at a temperature of not more than 50° C. so that the ground mixture is in the form of particles having a median diameter which varies from 50 μm to 100 μm,
   (c) extruding the mixture through an extruder, equipped with one or more dies, so as to obtain rods, and
   (d) spheronizing the rods,
   wherein the prepared cores are homogeneous hydrophilic active principle cores of granules intended for animal nutrition.

2. Process according to claim 1, wherein a preliminary co-grinding of the mixture is performed so that at least 50% of ground particles of median ingredients of the mixture are less than 100 μm in size.

3. Process according to claim 1, wherein a preliminary co-grinding of the mixture is performed so that not more than 50% of ground particles of median ingredients of the mixture are between 100 and 200 μm in size.

4. Process according to claim 1, in which said cores comprise a hydrophilic active ingredient selected from the group consisting of lysine, arginine and tyrosine, and salts and esters thereof.

5. Process according to claim 1, wherein the meltable binder is stearic acid.

6. Process according to claim 1, in which said cores comprise a plasticizer selected from the group consisting of cellulose and derivatives thereof.

7. Process according to claim 1, wherein the extruder is a single-screw or twin-screw extruder.

8. Process according to claim 1, wherein the mixture does not contain water.

9. Process according to claim 8, wherein the starch is present in the mixture in an amount that doubles the extrusion rate of the plurality of extrudates.

10. Process according to claim 9, wherein the starch is present in an amount of about 6% by weight of the cores.

11. Process according to claim 1, wherein the plasticizer is a derivative of cellulose.

12. Process according to claim 11, wherein the plasticizer is present in an amount of 2% by weight of the cores.

13. Process according to claim 1, wherein the starch is present in an amount of about 6% by weight of the cores, and the plasticizer is present in an amount of about 2% by weight of the cores.

14. Process according to claim 13, wherein the meltable binder is stearic acid and is present in an amount of not more than 12% by weight of the cores.

15. Process according to claim 13, wherein the mixture does not contain water.

* * * * *